(12) United States Patent
Chin

(10) Patent No.: US 7,677,328 B2
(45) Date of Patent: Mar. 16, 2010

(54) MULTIPLE FLEX-SHAFT ADAPTER FOR ELECTRIC DRILL

(76) Inventor: David Bunthean Chin, 2728 Crystal Falls Rd., Lexington, KY (US) 40509

(*) Notice: Subject to any disclaimer, the term of this patent is extended or adjusted under 35 U.S.C. 154(b) by 64 days.

(21) Appl. No.: 11/879,540

(22) Filed: Jul. 17, 2007

(65) Prior Publication Data

US 2009/0022562 A1 Jan. 22, 2009

(51) Int. Cl.
*B25F 3/00* (2006.01)
(52) U.S. Cl. .................................. 173/217; 173/216
(58) Field of Classification Search ............ 173/217, 173/216; 408/239 A, 1 BD; 132/75.8; 279/143
See application file for complete search history.

(56) References Cited

U.S. PATENT DOCUMENTS

| | | | |
|---|---|---|---|
| 910,789 A | 1/1909 | Cunningham | |
| 2,765,013 A | 10/1956 | Pedersen | |
| 2,858,703 A | 11/1958 | Willcox | |
| 2,859,627 A | 11/1958 | Gallop, Jr. | |
| 3,006,395 A * | 10/1961 | Dye | 81/177.4 |
| 3,712,751 A | 1/1973 | Dietrich | |
| 4,085,337 A | 4/1978 | Moeller | |
| 4,241,773 A * | 12/1980 | Personnat | 81/177.4 |
| 4,320,544 A | 3/1982 | Bryant et al. | |
| 4,399,723 A | 8/1983 | Marleau | |
| 4,572,038 A | 2/1986 | Graham | |
| 4,653,356 A | 3/1987 | Golden | |
| 4,727,941 A | 3/1988 | Fulton | |
| 4,729,698 A | 3/1988 | Haddon | |
| 4,791,690 A | 12/1988 | Kuang-Wu | |
| 4,945,790 A | 8/1990 | Golden | |
| 4,976,175 A * | 12/1990 | Hung | 81/439 |
| 4,996,761 A | 3/1991 | Crain, Jr. | |
| 5,065,498 A * | 11/1991 | McKenzie | 483/57 |
| 5,451,127 A * | 9/1995 | Chung | 408/20 |
| 5,595,250 A | 1/1997 | Bourke | |
| 5,893,689 A | 4/1999 | Juhasz | |
| 6,264,211 B1 | 7/2001 | Granado | |
| 6,293,320 B1 | 9/2001 | McGregor, II | |
| 6,352,127 B1 * | 3/2002 | Yorde | 173/216 |
| 6,354,176 B1 | 3/2002 | Nordlin | |
| 6,543,926 B2 | 4/2003 | Sherez | |
| 7,131,180 B2 | 11/2006 | Kopras et al. | |
| 2001/0045550 A1 | 11/2001 | Reilly et al. | |
| 2002/0024886 A1 | 2/2002 | Sherez | |
| 2003/0102002 A1 * | 6/2003 | Cho | 132/73.6 |
| 2005/0200087 A1 * | 9/2005 | Vasudeva et al. | 279/143 |
| 2008/0279645 A1 * | 11/2008 | Bae | 408/198 |

* cited by examiner

*Primary Examiner*—Brian D Nash
(74) *Attorney, Agent, or Firm*—King & Schickli, PLLC

(57) ABSTRACT

A multiple flex-shaft adapter coupled to an electric drill has a housing assembly attaching to the drill at one end and to a plurality of flex-shafts at an opposite end. The flex-shafts have specialized drill bits attached thereto for performing different nail operations. A gear assembly is located in the housing assembly for transferring power from the drill to the plurality of flex-shafts. Preferably, an operator selects a switching member corresponding to a desired one of the plurality of flex-shafts and pushes the member horizontally into the housing. After entering the housing assembly, the switching member rises up towards the gear assembly. Subsequently, the operator inserts the desired one of the plurality of flex-shafts into the housing assembly through a receiver to engage the gear assembly. In turn, power is transferred from the drill through the gear assembly to the desired one.

12 Claims, 19 Drawing Sheets

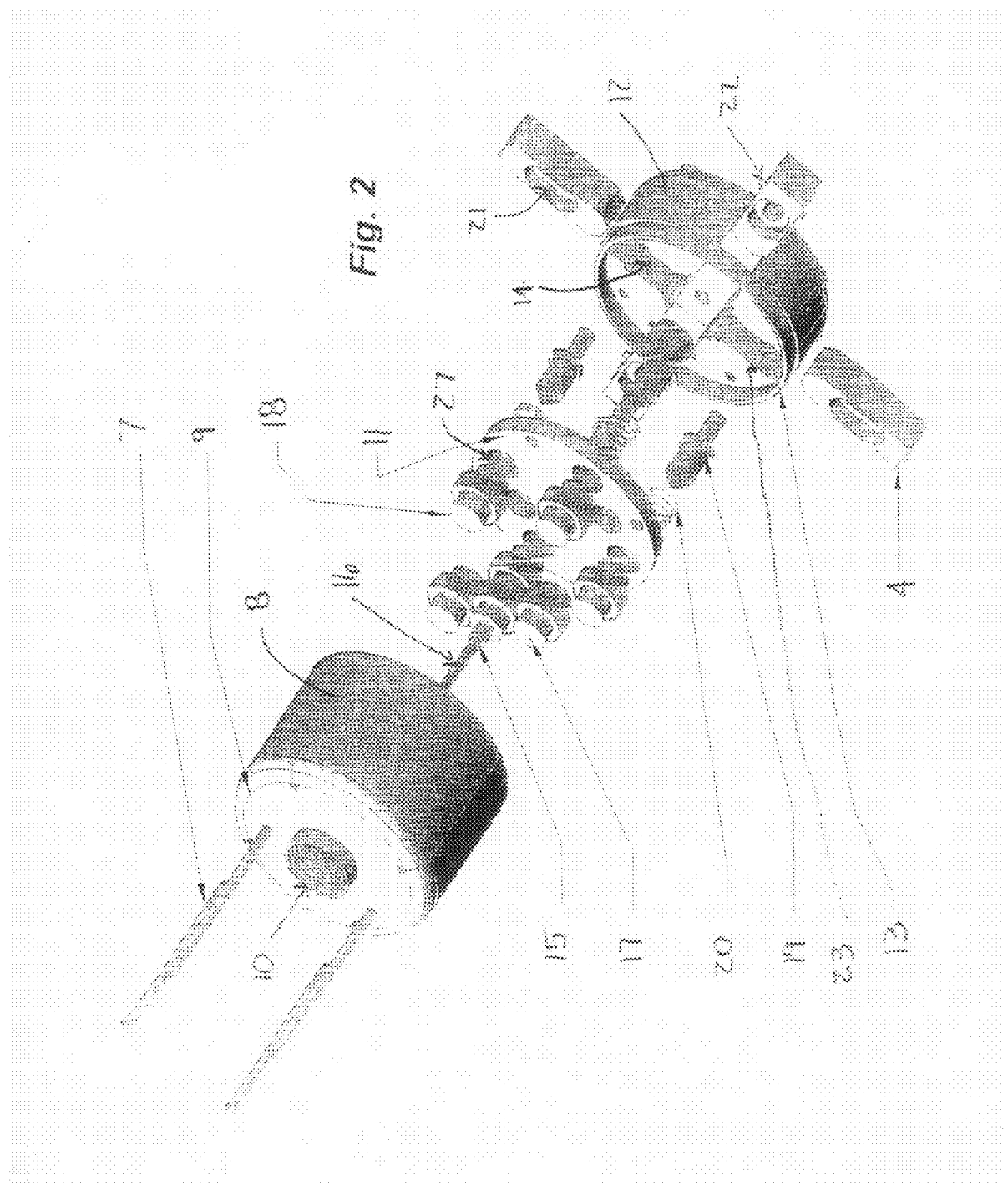

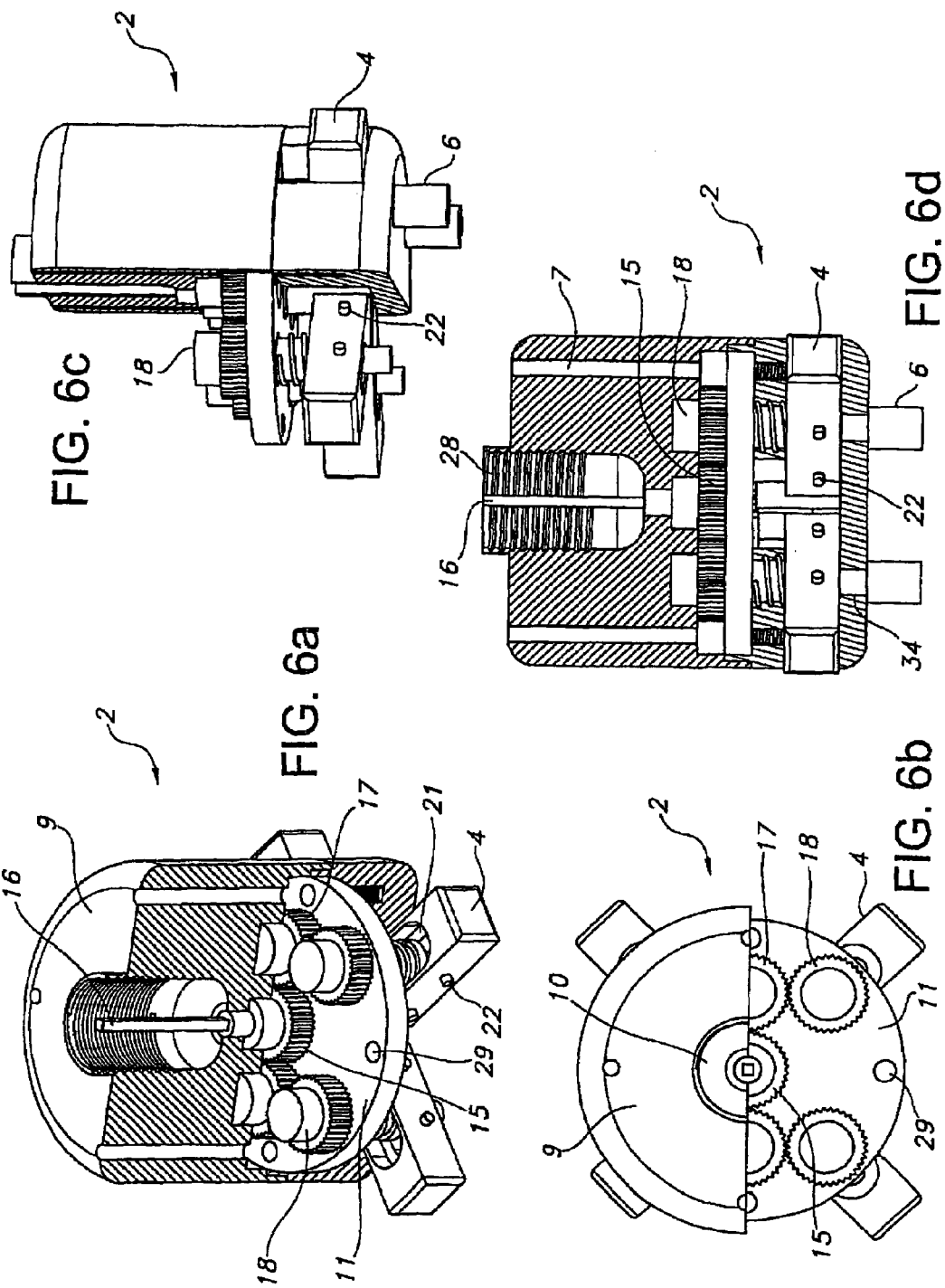

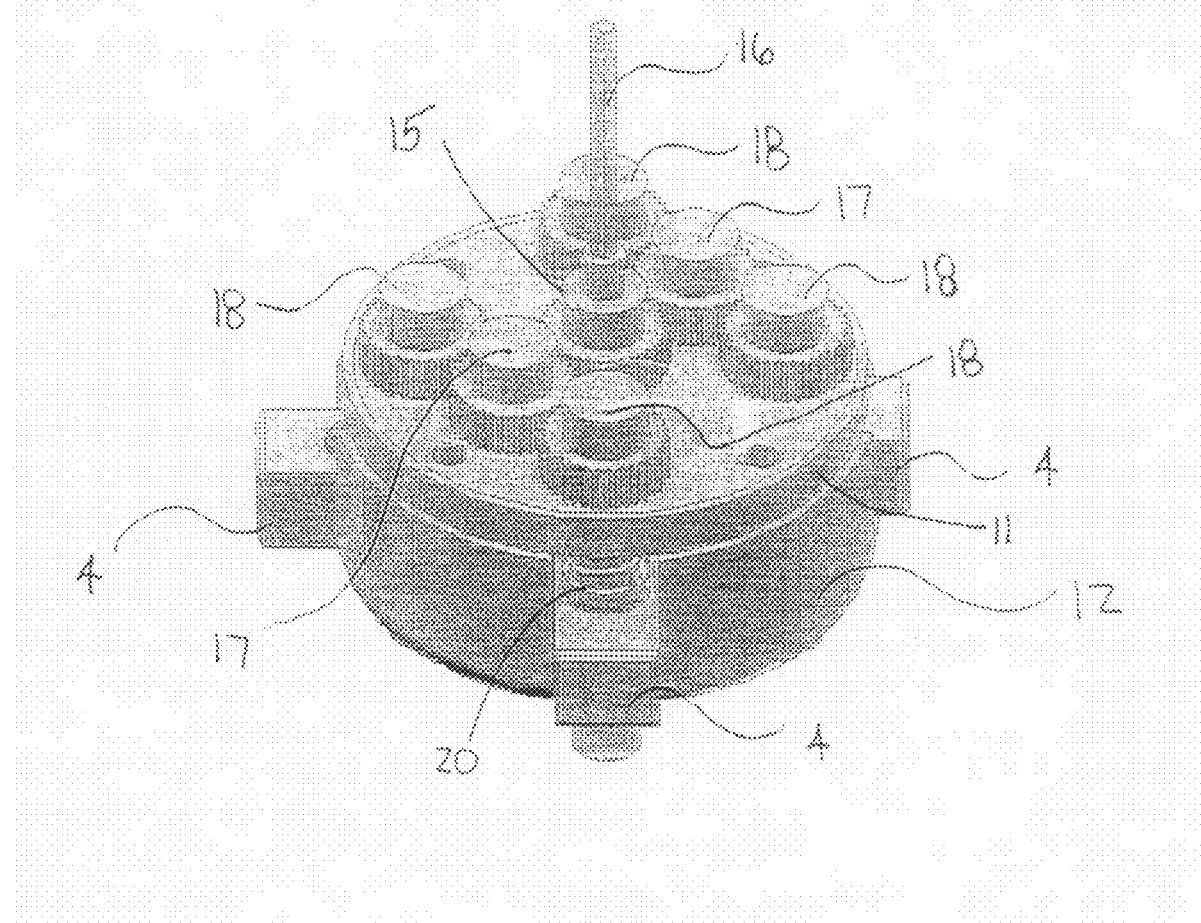

MULTIPLE FLEX-SHAFT ADAPTER FOR ELECTRIC DRILL

TECHNICAL FIELD

The present invention relates generally to adapters for electric drills. In particular, it relates to an apparatus and method for a multiple flex-shaft adapter for an electric drill to allow an operator to perform multiple operations without changing a drill bit attached to the drill.

BACKGROUND OF THE INVENTION

Electric drills and other rotary power tools are commonly used in numerous applications, such as in the fields of cosmetics, dentistry and jewelry. For example, cosmetologists or nail technicians use electric drills to perform manicures and pedicures. Specifically, they use electric drills with specialized drill bits or tips attached to a drill chuck to remove incremental quantities of natural or artificial nail surfaces.

Conventional electric drills have an electrical power source, which drives a motor in the drill to rotate a chuck at an output end. The chuck is adapted to receive and hold a variety of drill bits. In the field of cosmetology, nail technicians use electric drills to perform a number of different functions, such as filing, shaping, polishing and buffing natural and artificial nails. Each separate function usually requires use of a different drill bit. As a result, nail technicians are constantly changing, removing and replacing the drill bits to perform different operations.

Generally, it is time-consuming and inefficient to change the drill bit numerous times while performing the various operations related to a manicure or pedicure. An alternative to continuously changing the drill bit on the chuck is to have multiple electric drills with different drill bits available for use. This alternative, however, is undesirable because it is expensive to acquire multiple electric drills. Moreover, multiple electric drills occupy a large quantity of limited work space in the salon or work station.

Accordingly, the art of cosmetics and other related fields have a need for minimizing the time-consuming process of constantly changing the drill bit on electric drills. In addition, they have a need for minimizing the expense and spacial restrictions related to the use of multiple electric drills in the work space.

SUMMARY OF THE INVENTION

The above-mentioned and other problems become solved by applying the principles and teachings associated with the hereinafter described multiple flex-shaft adapter for electric drill.

In a basic sense, the adapter connects to an electric drill at one end and to a plurality of flex-shafts at an opposite end. The plurality of flex-shafts are attached to specialized drill bits used in salons to perform different nail care operations. Accordingly, the adapter will increase the efficiency of nail technicians because it is not necessary to constantly change the drill bit to perform different operations. Further, nail technicians can reduce their costs because multiple electric drills are not required to connect to different drill bits.

In one embodiment, the invention teaches an adapter having a housing that connects at one end to an electric drill and connects at an opposite end to a plurality of flex-shafts. Specialized drill bits for performing specific nail functions are connected at the opposite end of the flex-shafts. An operator selects a switching member corresponding to the flex-shaft and drill bit desired for a specific function and pushes the member into the housing wherein the member rises up causing a lower gear to contact a corresponding upper gear. Subsequently, the operator inserts the flex-shaft into the bottom of the housing through a receiver to overcome a biasing mechanism allowing the lower gear to mate with the upper gear. Finally, power is transferred from the drill through the gear assembly to the flex-shaft.

In other aspects of the invention, a block is positioned between the plurality of switching members. The block prevents the switching members and corresponding flex-shafts not selected by the operator from engaging the gear assembly and, therefore, acquiring power from the drill. The gear assembly has a main gear, a pair of reverse gears and a plurality of upper and lower gears. The main gear connects to a post connecting to a drill chuck attached to the drill. As the drill chuck receives power from the drill, the post rotates the main gear. The pair of reverse gears are engaged to the main gear and are also engaged to the plurality of upper gears having corresponding lower gears. In turn, the rotation of the main gear causes the reverse gears and the upper gears and corresponding lower gears to rotate. As a result, power is ultimately transferred to the flex-shafts.

These and other embodiments, aspects, advantages, and features of the present invention will be set forth in the description which follows, and in part will become apparent to those of ordinary skill in the art by reference to the following description of exemplary embodiments of the invention and referenced drawings or by practice of the invention. The aspects, advantages, and features of the invention are realized and attained according to the following description and as particularly pointed out in the appended claims.

BRIEF DESCRIPTION OF THE DRAWINGS

The accompanying drawings incorporated in and forming a part of the specification, illustrate several aspects of the present invention, and together with the description serve to explain the principles of the invention. In the drawings:

FIG. 2 is an exploded perspective view in accordance with one embodiment of the present invention of the multiple flex-shaft adapter assembly;

FIG. 6a is a perspective partial cross-sectional view in accordance with one embodiment of the present invention of the top of the adapter;

FIG. 6b is a top partial cross-sectional view in accordance with one embodiment of the present invention of the adapter;

FIG. 6c is a perspective partial cross-sectional view in accordance with one embodiment of the present invention of the side of the adapter;

FIG. 6d is a cross-sectional view in accordance with one embodiment of the present invention of the front of the adapter with a drill chuck attached to a rod connected to a main gear;

FIG. 16 is a perspective view in accordance with one embodiment of the present invention of the bottom portion of the housing with the washer and the gear assembly mounted thereon;

DETAILED DESCRIPTION OF THE DRAWINGS

In the following detailed description of the drawings, reference is made to the accompanying drawings that form a part hereof, and in which is shown by way of illustration, specific embodiments in which the invention may be practiced. These embodiments are described in sufficient detail to enable those skilled in the art to practice the invention and like numerals represent like details in the various figures. Also, it is to be understood that other embodiments may be utilized and that process or other changes may be made without departing from the scope of the present invention. The following detailed description is, therefore, not to be taken in a limiting sense, and the scope of the present invention is defined only by the appended claims and their equivalents. In accordance with the present invention, a multiple flex-shaft adapter for electric drill is hereinafter described.

Figure 1:
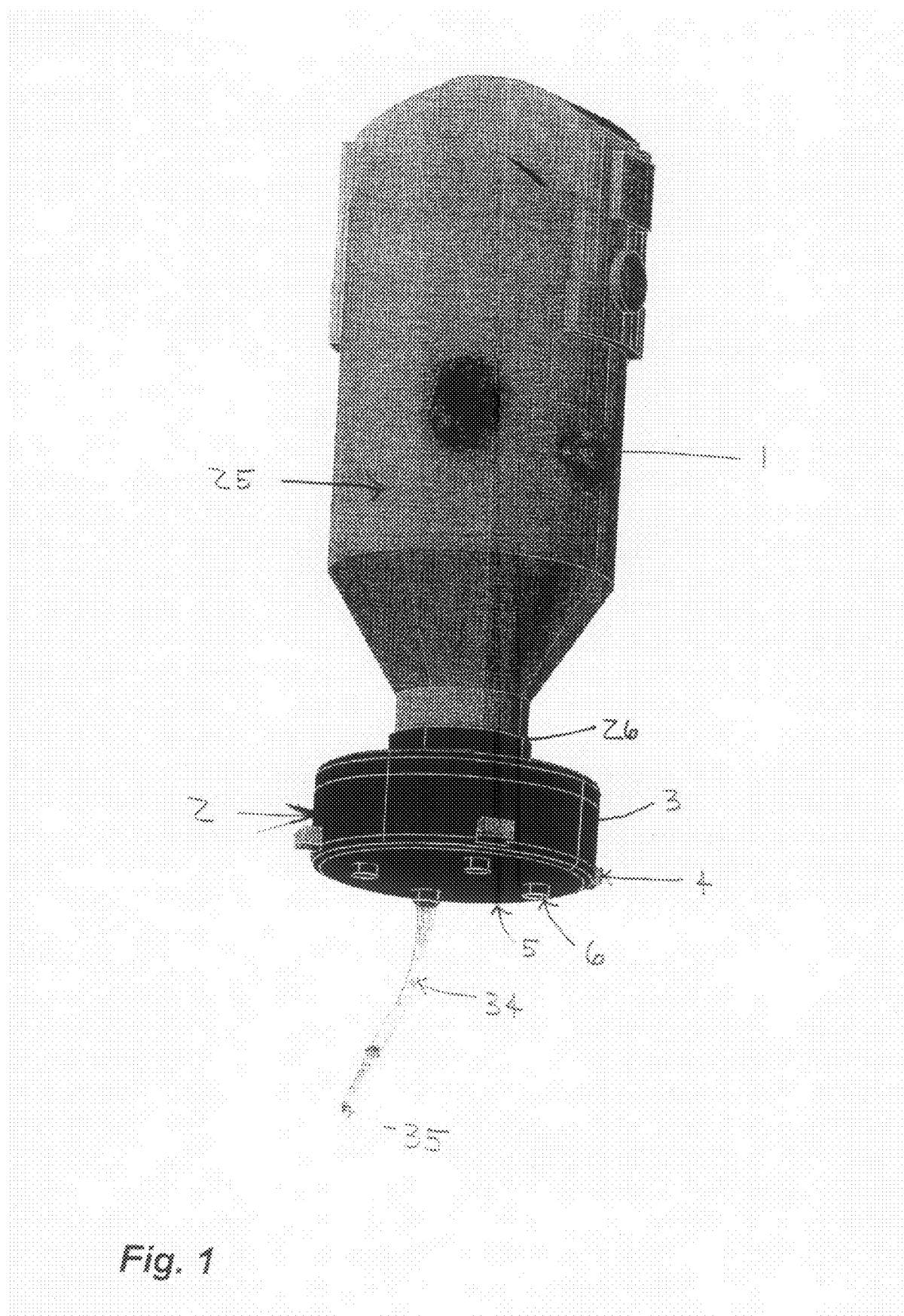
FIG. 1 is a perspective view in accordance with one embodiment of the present invention of an electric drill with a multiple flex-shaft adapter attached thereto.
Figure 3A:
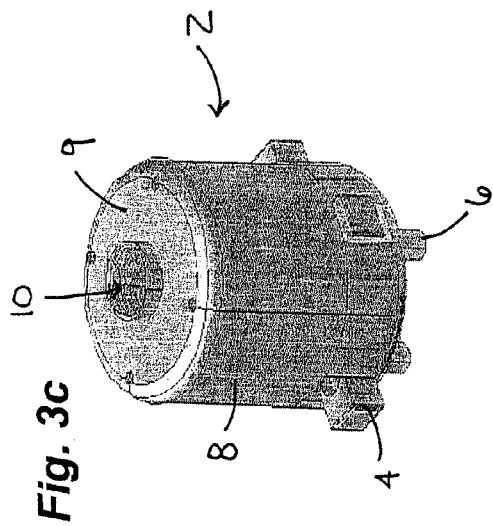
FIG. 3a is a front view in accordance with one embodiment of the present invention of the adapter.
Figure 3B:
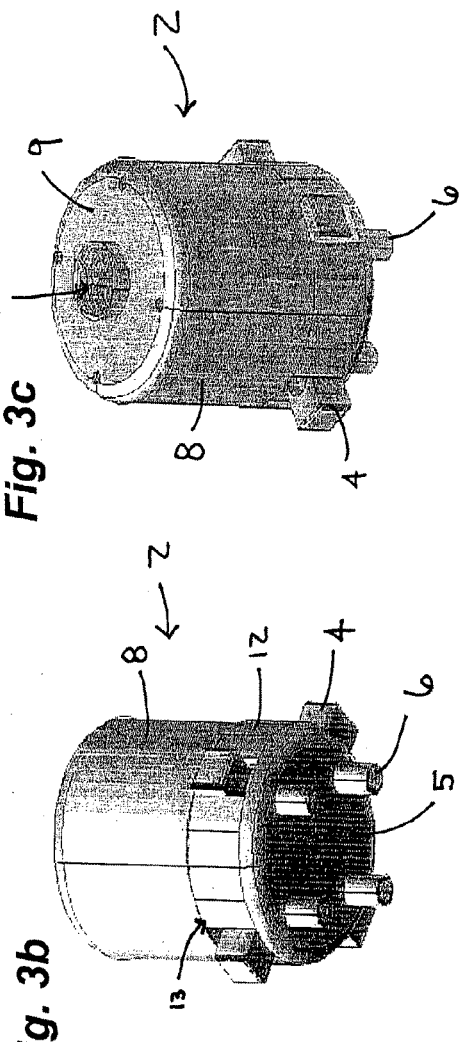
FIG. 3b is a perspective view in accordance with one embodiment of the present invention of the bottom of the adapter.
Figure 3C:
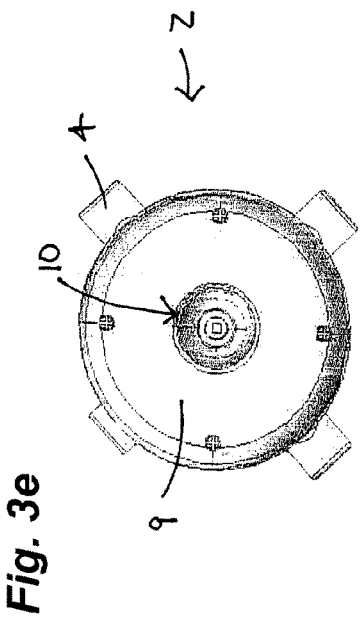
FIG. 3c is a perspective view in accordance with one embodiment of the present invention of the top of the adapter.
Figure 3D:
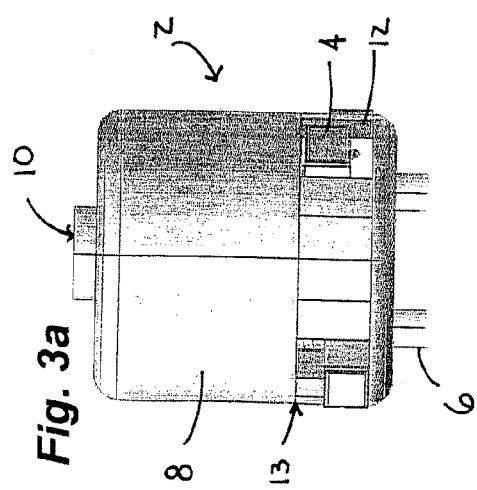
FIG. 3d is a bottom view in accordance with one embodiment of the present invention of the adapter.
Figure 3E:
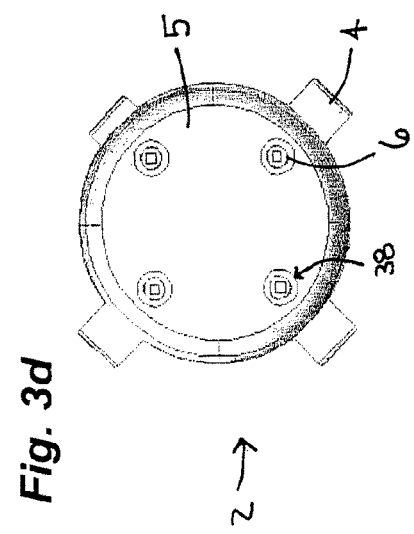
FIG. 3e is a top view in accordance with one embodiment of the present invention of the adapter.
Figure 4A:
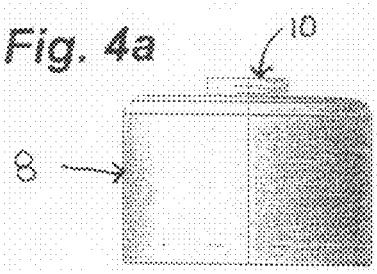
FIG. 4a is a front view in accordance with one embodiment of the present invention of a top portion of a housing of the adapter.
Figure 4B:
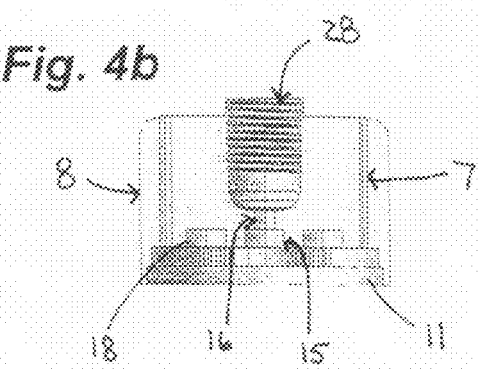
FIG. 4b is a cross-sectional view in accordance with one embodiment of the present invention of the top portion of the housing of the adapter.
Figure 4C:
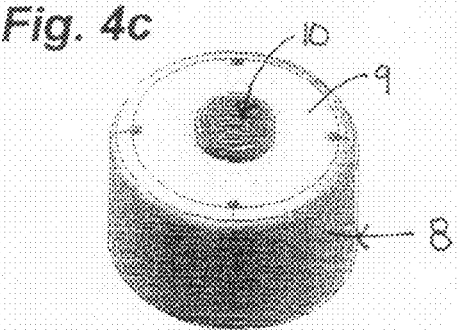
FIG. 4c is a perspective view in accordance with one embodiment of the present invention of the top of the top portion of the housing of the adapter.
Figure 4D:
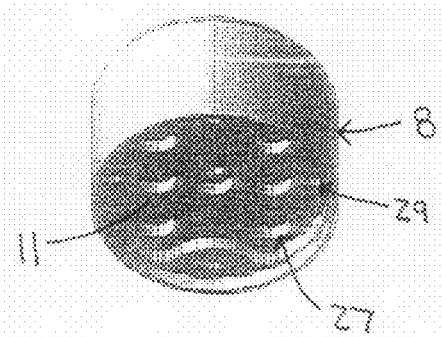
FIG. 4d is a perspective view in accordance with one embodiment of the present invention of the bottom of the top portion of the housing of the adapter.
Figure 5A:
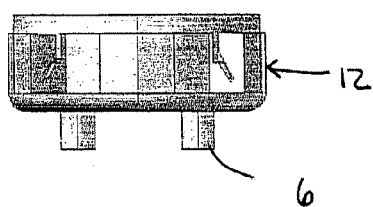
FIG. 5a is a front view in accordance with one embodiment of the present invention of a bottom portion of a housing of the adapter.
Figure 5B:
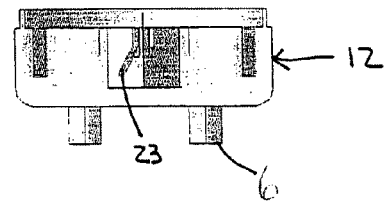
FIG. 5b is a cross-sectional view in accordance with one embodiment of the present invention of the bottom portion of the housing of the adapter.
Figure 5C:
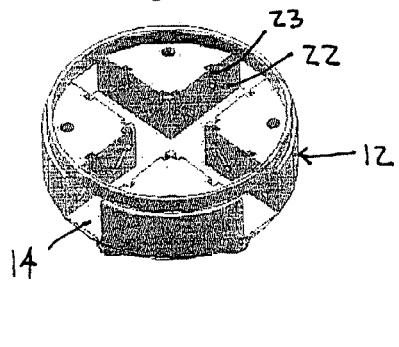
FIG. 5c is a perspective view in accordance with one embodiment of the present invention of the top of the bottom portion of the housing of the adapter with a plurality of screws from a plurality of members (not shown) fitted in a plurality of slots.
Figure 5D:
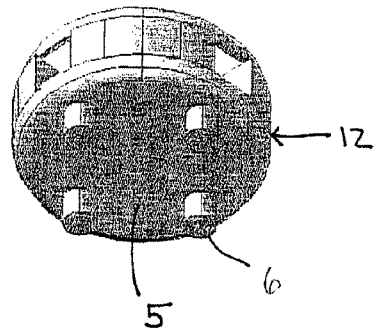
FIG. 5d is a perspective view in accordance with one embodiment of the present invention of the bottom of the bottom portion of the housing of the adapter.
Figure 7A:
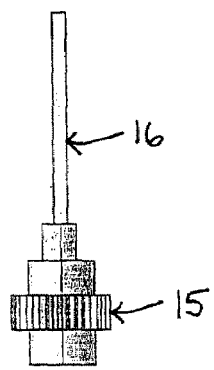
FIG. 7a is a front view in accordance with one embodiment of the present invention of a main gear and a rod connected to said gear.
Figure 7B:
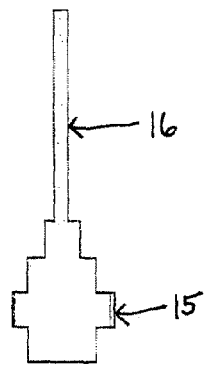
FIG. 7b is cross-sectional view in accordance with one embodiment of the present invention of the main gear and the rod connected to said gear.
Figure 7C:
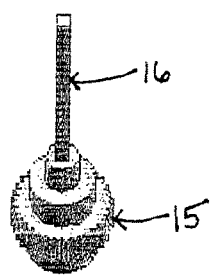
FIG. 7c is a perspective view in accordance with one embodiment of the present invention of the top of the main gear and the rod connected to said gear.
Figure 7D:
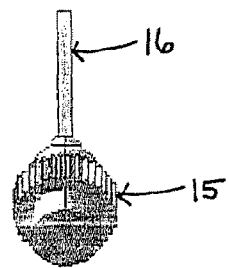
FIG. 7d is a perspective view in accordance with one embodiment of the present invention of the bottom of the main gear and the rod connected to said gear.
Figure 8A:
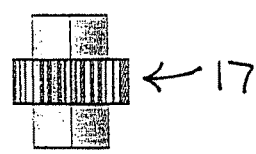
FIG. 8a is a front view in accordance with one embodiment of the present invention of a reverse gear.
Figure 8B:
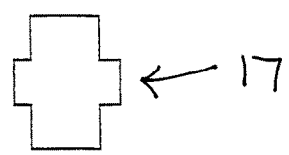
FIG. 8b is cross-sectional view in accordance with one embodiment of the present invention of the reverse gear.
Figure 8C:
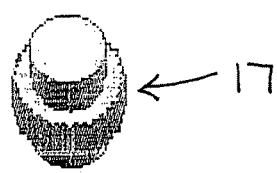
FIG. 8c is a perspective view in accordance with one embodiment of the present invention of the top of the reverse gear.
Figure 8D:
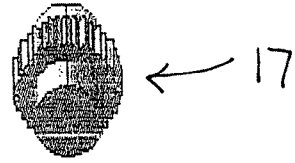
FIG. 8d is a perspective view in accordance with one embodiment of the present invention of the bottom of the reverse gear.
Figure 9A:
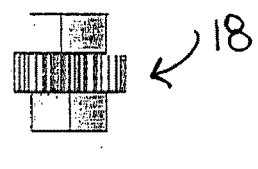
FIG. 9a is a front view in accordance with one embodiment of the present invention of an upper gear.
Figure 9B:
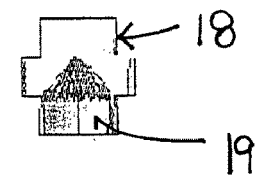
FIG. 9b is cross-sectional view in accordance with one embodiment of the present invention of the upper gear.
Figure 9C:
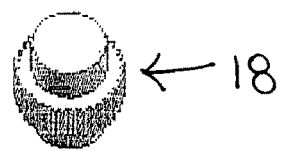
FIG. 9c is a perspective view in accordance with one embodiment of the present invention of the top of the upper gear.
Figure 9D:
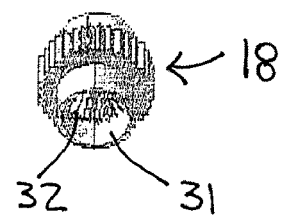
FIG. 9d is a perspective view in accordance with one embodiment of the present invention of the bottom of the upper gear.
Figure 10A:
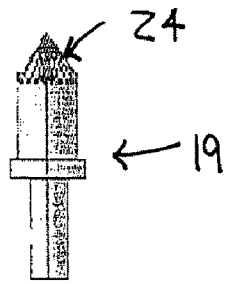
FIG. 10a is a front view in accordance with one embodiment of the present invention of a lower gear.
Figure 10B:
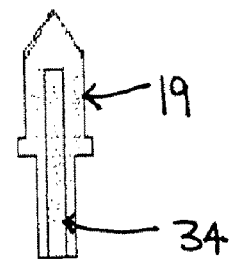
FIG. 10b is a cross-sectional view in accordance with one embodiment of the present invention of the lower gear.
Figure 10C:
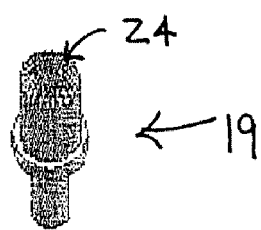
FIG. 10c is a perspective view in accordance with one embodiment of the present invention of the top of the lower gear.
Figure 10D:
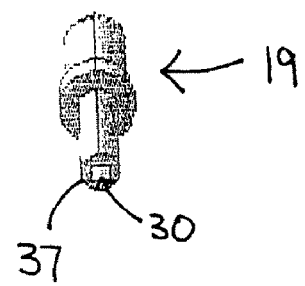
FIG. 10d is a perspective view in accordance with one embodiment of the present invention of the bottom of the lower gear.
Figure 11B:
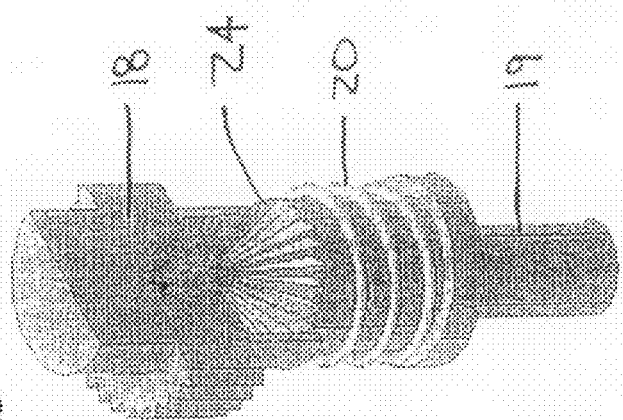
FIG. 11b is a perspective partial cross-sectional view in accordance with one embodiment of the present invention of the upper gear mated with the lower gear.
Figure 11A:
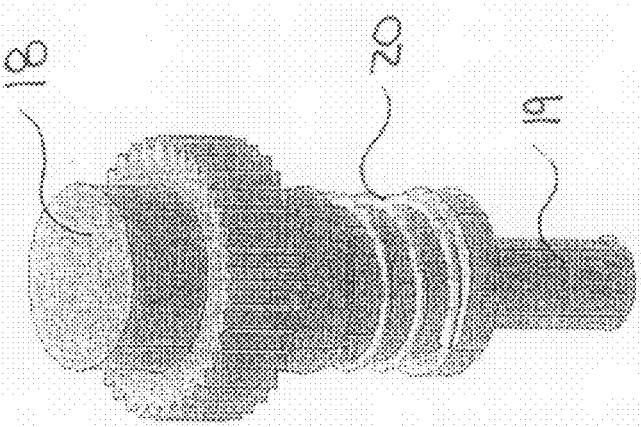
FIG. 11a is a perspective view in accordance with one embodiment of the present invention of the upper gear mated with the lower gear.

With reference to FIGS. 1 and 2, a multiple flex-shaft adapter 2 according to one embodiment of the present invention is attached to an electric drill 1. The drill 1 has a body 25 that is connected by a cord (not shown) to a power supply (not shown). The adapter 2 is coupled to the drill 1 at an end 26 of the drill where a drill chuck 28 (shown in FIG. 4b) is located on the drill 1.

The adapter 2 has a housing assembly 3 formed of a rigid material such as plastic. A plurality of receivers 6 are symmetrically connected to a bottom face 5 of the adapter 2. The receivers 6 extend from the bottom face 5 of the adapter 2 wherein a plurality of flex-shafts 34 (for simplicity only one flex-shaft is shown) may be inserted into the receivers 6. In the preferred embodiment, four receivers 6 extend from the adapter 2 capable for connection to four flex-shafts 34. The four flex-shafts 34 are coupled to four electric drill bits 35 (only one electric drill bit is shown), such as a carbide bit, diamond bit, mandrel bit, sanding band or other specialized nail bits commonly used by nail technicians for performing specialized cosmetic functions for hands and fingernails. Although the flex-shafts have been described for use by a nail technicians, it should be understood that the adapter may be fitted with other types of bits for use in other fields, such as dentistry, jewelry or related fields utilizing multiple drill bits.

During use, an operator selects a desired nail bit 35 for its specific function. The operator attaches the nail bit 35 to the flex-shaft 34. It should be noted that only one flex-shaft and corresponding nail bit are shown, but the adapter 2 is capable of having at least four flex-shafts attached to it. In an embodiment wherein more than four flex-shafts are capable for attachment to the adapter, the housing of the adapter may be larger than the embodiment illustrated in the diagrams. The operator pushes a switching member 4 corresponding to the desired flex-shaft horizontally into the housing 3. The member 4 slides along a longitudinal recess 14 in the housing 3 until a pair of rods 22 located on the member 4 fit into a guiding channel 23 located in the housing. The rods 22 slide upward along the channel 23 causing the member 4 to rise. As the member 4 rises, a lower gear 19 extending through a slot 21 on the member 4 rises with the member 4 to contact a corresponding upper gear 18. In turn, the flex-shaft 34 is inserted into the receiver 6 corresponding to the raised member 4 allowing the lower gear 19 to mate with the upper gear 18 by overcoming a biasing mechanism 20. Subsequently, power is transferred through the gear assembly to the desired flex-shaft 34 for operation of the drill bit 35. To facilitate rotation, skilled artisans may also find it useful to position various bearings or other slip-inducing devices with the gearing.

This invention offers a number of advantages not disclosed in the prior art. Specifically, the adapter enables an operator to perform multiple operations without changing the drill bit because four or more drill bits may be attached to the flex-shafts attached to the adapter. Further, the adapter eliminates the necessity of having multiple drills in a work station and, therefore, reduces the expenses associated with acquiring multiple drills.

The housing assembly 3 of the adapter 2 is formed of a top portion 8 and a bottom portion 12 assembled together through attachment or connection at interface 13. In the preferred embodiment, four bolts 7 extend vertically through a washer 11 connecting the top portion 8 to the bottom portion 12. The shape of the top portion 8 is generally cylindrical. The top portion 8 is primarily hollow for housing a number of the elements discussed in more detail below. The top portion 8 has a threaded opening 10 located on a top face 9 of the adapter 2 for receiving the drill 1. The shape of the bottom portion 12 is generally cylindrical. The bottom portion 12 has diametrically opposed longitudinal recesses 14. The pair of guiding channels 23 are located in each of the recesses 14. The pair of rods 22 extend perpendicular to the plurality of switching members 4 fitting into the channels 23. The rods 22 slide upward along the path of the channels 23 causing the member 4 to rise.

The washer 11 has a plurality of openings 27 to secure a gear assembly having a main gear 15, a pair of reverse gears 17 and a plurality of upper gears 18 and lower gears 19. The washer 11 is positioned in the housing 3 between the top portion 8 and the bottom portion 12. The main gear 15 is located at the center of the washer 11 attached to a post 16 extending vertically through the top portion 5 to engage the drill chuck 28. The post 16 is attached to the drill chuck 28 in the location where the drill chuck 28 generally attaches to the drill bit 35. The post 16 is preferably rectangular so that it may freely rotate about its longitudinal axis when power is applied to the drill chuck 28. As will be further described below, the main gear 15 operates in conjunction with the reverse gears 17 and upper gears 18 to transfer power from the drill 1 to the desired flex-shaft 34 when a specific member 4 is selected.

Referring to FIGS. 3a-3e, the adapter 2 in accordance with one embodiment of the present invention is shown. The switching member 4' is shown inserted into the housing 3 wherein the member 4' is in a raised position compared to the other members 4. The receivers 6 are formed of a rigid material such as plastic and are molded to the bottom face 5 of the adapter 2. The receivers 6 are cylindrical with a circular opening 36 at the bottom face 5 of the adapter 2 wherein the flex-shafts 34 are inserted and connected to the lower gears 19. In an alternative embodiment, the adapter 2 does not have receivers. Rather, the flex-shafts 34 insert directly into the lower gears 19 through openings (not shown) at the bottom face 5 of the adapter 2.

With reference to FIGS. 4a-4d, the top portion 8 of the housing 3 in accordance with one embodiment of the present invention is shown. The top portion 8 connects to the drill 1 through the threaded opening 10. The drill chuck 28 connects to the post 16 attached to the main gear 15. The washer 11 is positioned at the end of the top portion 8 opposite the drill connection location.

Turning to FIGS. 5a-5d, the bottom portion 12 of the housing 3 in accordance with one embodiment of the present invention is shown. The bottom portion 12 has two longitudinal recesses 14 running perpendicular to each other dividing the bottom portion into four triangular shaped quadrants. The pair of guiding channels 23 located in each of the recesses 14 is illustrated. As shown, the rods 22 extending from the switching members 4 fit into the guiding channels 23 when the member 4 is pushed into the housing 3 and travels along the recess 14. As the rods 22 slide upward along the channel 23, the member 4 rises causing the lower gear 19 to contact the upper gear 18.

Figure 12B:
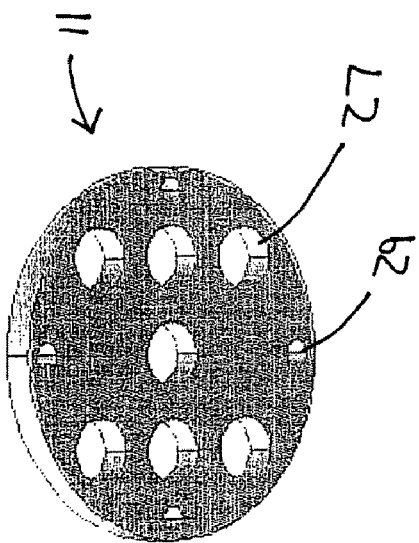
FIG. 12b is a perspective view in accordance with one embodiment of the present invention of the bottom of the washer.
Figure 12A:
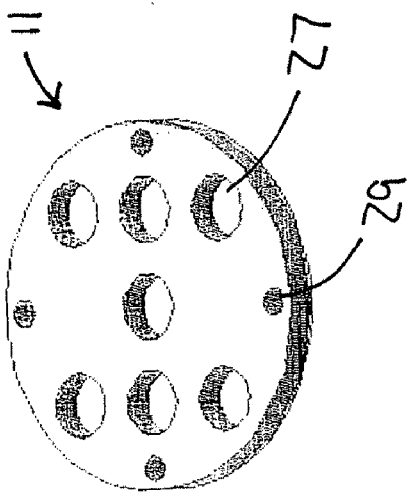
FIG. 12a is a perspective view in accordance with one embodiment of the present invention of the top of a washer.

With reference to FIGS. 12a and 12b, the washer 11 in accordance with one embodiment of the present invention is shown. The washer 11 has a plurality of openings 27 to secure the gear assembly (not shown). Further, the washer 11 has a plurality of holes 29 located at 0°, 90°, 180° and 270° to allow the bolts 7 to extend through to connect the top portion 8 to the bottom portion 12 of the housing 3.

Referring to FIGS. 9a-9d, the upper gears 18 in accordance with one embodiment of the present invention are shown. Each of the upper gears 18 have a circular open bottom 31 with a threaded portion 32 to mate with the corresponding lower gear 19. As illustrated in FIGS. 10a-10d, the lower gears 19 in accordance with one embodiment of the present invention have a spear-like head 24 with oval shape to mate with the corresponding upper gear 18. Further, the lower gears 19 have a circular-shaped bottom 37 with a square opening 30 for insertion of the flex-shaft 34.

Figure 13B:
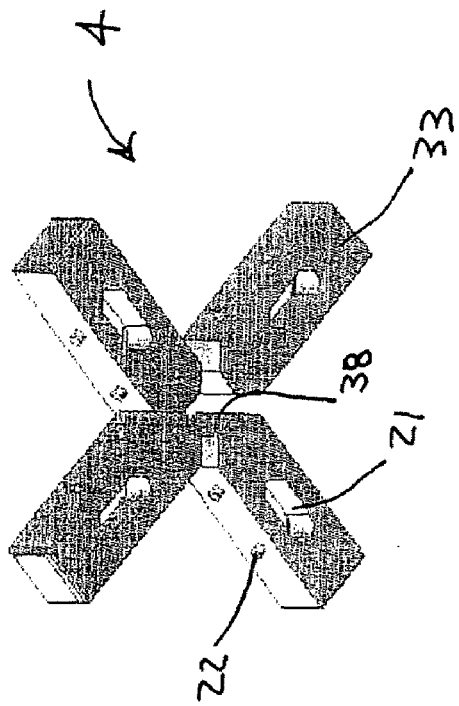
FIG. 13b is a perspective view in accordance with one embodiment of the present invention of the bottom of the plurality of members.
Figure 13A:
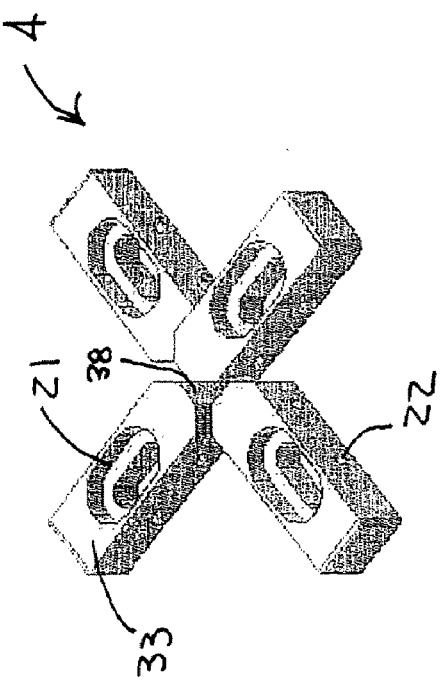
FIG. 13a is a perspective view in accordance with one embodiment of the present invention of the top of the plurality of members.
Figure 15A:
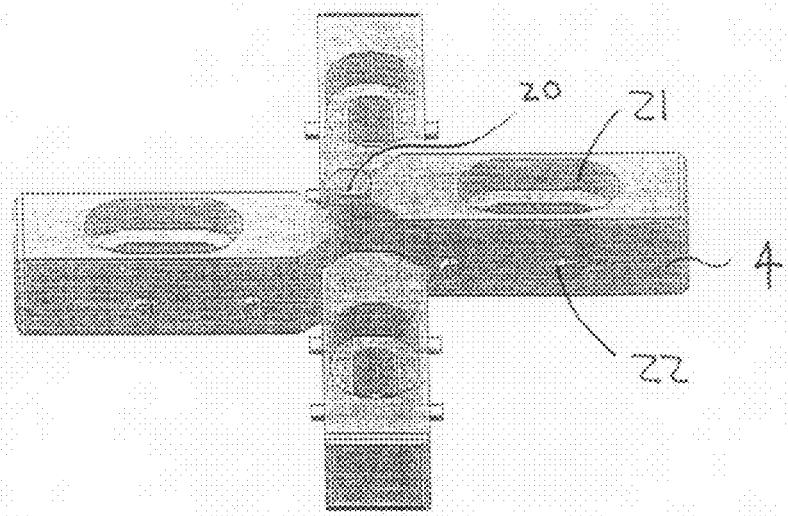
FIG. 15a is a perspective view in accordance with one embodiment of the present invention of a plurality of members and the block.
Figure 15B:
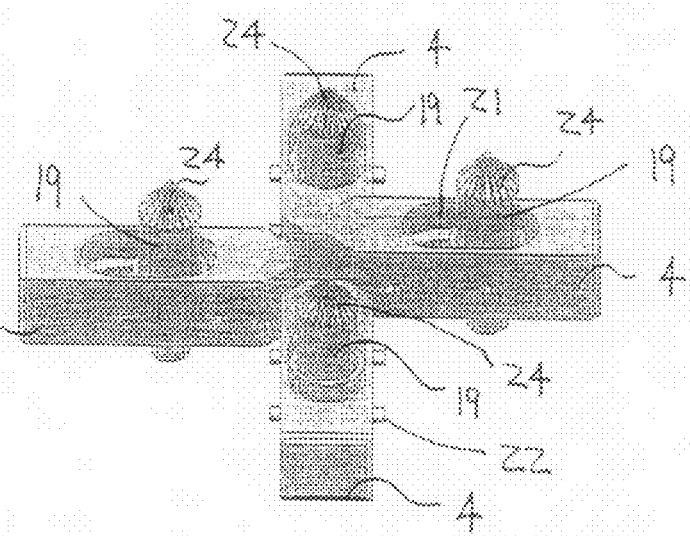
FIG. 15b is a perspective view in accordance with one embodiment of the present invention of the plurality of members with the plurality of lower gears extending through said members.
Figure 15C:
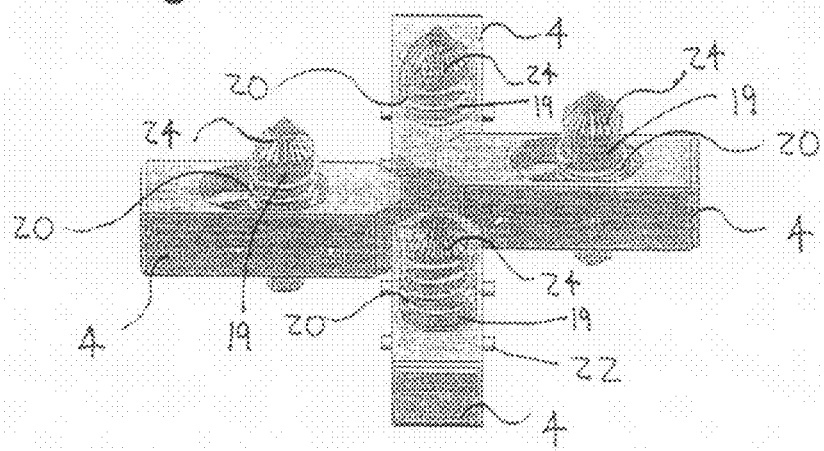
FIG. 15c is a perspective view in accordance with one embodiment of the present invention of the plurality of members with the plurality of lower gears with springs wrapped thereon extending through said members.
Figure 15D:
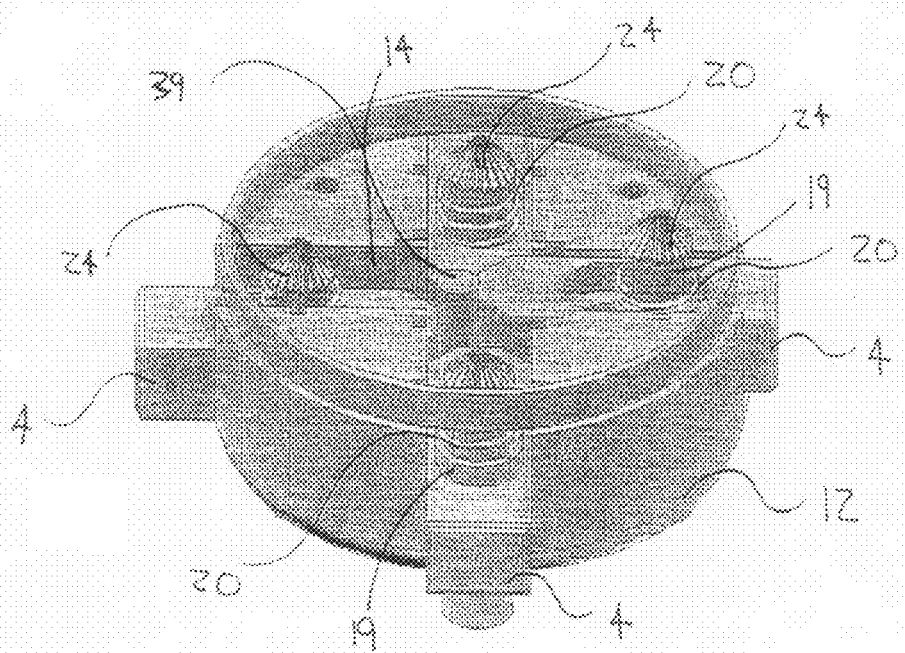
FIG. 15d is a perspective view in accordance with one embodiment of the present invention of the bottom portion of the housing.

With reference to FIGS. 13a and 13b, the switching members 4 in accordance with one embodiment of the present invention are illustrated. As previously discussed, the members 4 fit in the recesses 14 of the lower portion 12 of the housing 3. The members 4 have a rectangular body 33 that narrows to form three angled faces at an end enclosed in the housing 3. The most forward face 38 of the switch contacts the block 39 (shown in FIG. 15d). The members 4 have longitudinal oval slots 21 wherein the lower gears 19 (shown in FIG. 15b) extend vertically through said members 4 wherein at one end the lower gears 19 connect to the upper gears 18 when the member 4 is engaged and at an opposite end to the flex-shafts 34.

Figure 14A:
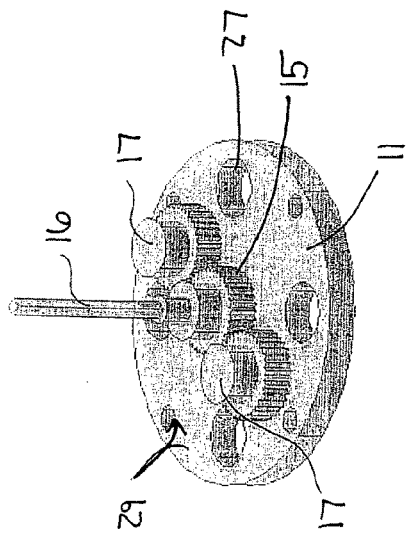
FIG. 14a is a perspective view in accordance with one embodiment of the present invention of the washer with the main gear mounted thereon.
Figure 14B:
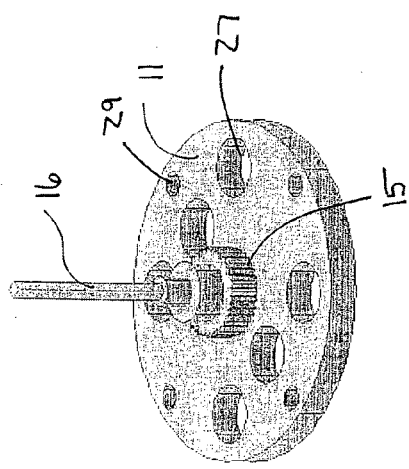
FIG. 14b is a perspective view in accordance with one embodiment of the present invention of the washer with the main gear and a pair of reverse gears mounted thereon.
Figure 14C:
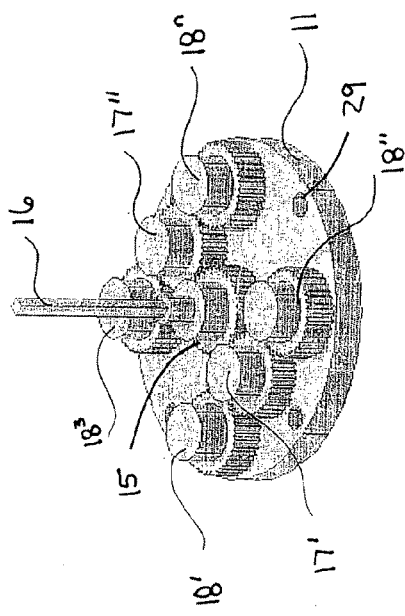
FIG. 14c is a perspective view in accordance with one embodiment of the present invention of the washer with the main gear, the pair of reverse gears mounted thereon and a plurality of upper gears mounted thereon.

With reference to FIGS. 14a-14c, the gear assembly in accordance with one embodiment of the present invention is shown. The main gear 15 connected to the post 16 is located on the center of the washer 11. A pair of reverse gears 17 are located on the washer 11. In the preferred embodiment, the first reverse gear 17' engages the main gear 15 between a first upper gear 18' and second upper gear 18" in which the first reverse gear 17' is also engaged with the first and second upper gears. Similarly, the second reverse gear 17" engages the main gear 15 between a third upper gear $18^3$ and fourth upper gear $18^n$ in which the second reverse gear 17" is also engaged with the third and fourth upper gear.

Figure 17A:
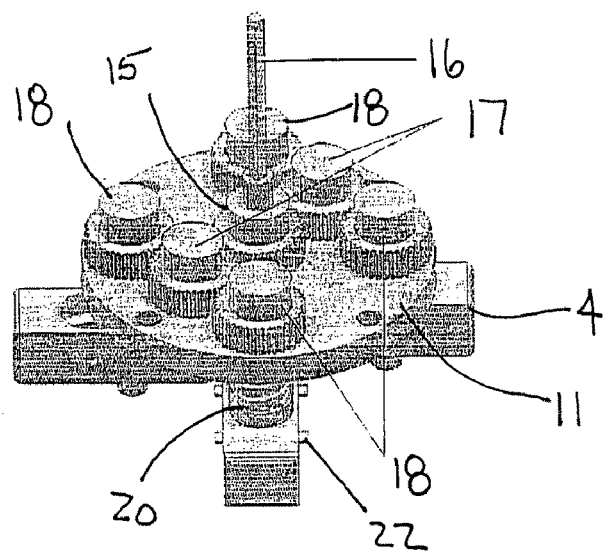
FIG. 17a is a perspective view in accordance with one embodiment of the present invention of the top of the gear assembly mounted on the washer and the plurality of members.
Figure 17B:
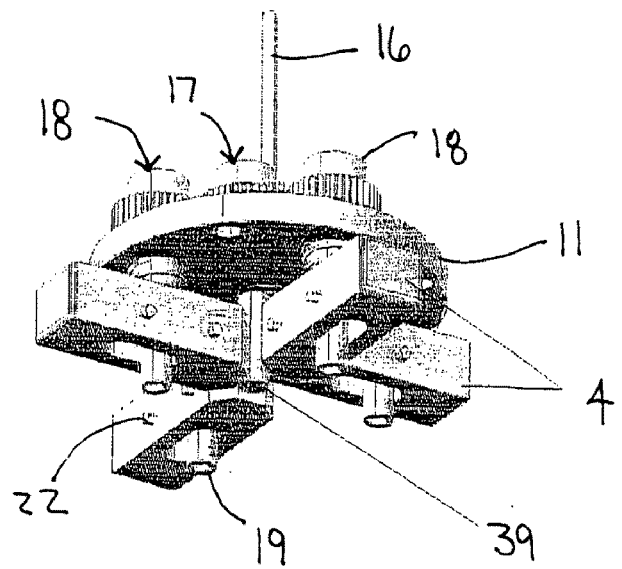
FIG. 17b is a perspective view in accordance with one embodiment of the present invention of the bottom of the gear assembly mounted on the washer and the plurality of members.

With reference to FIGS. 16, 17a and 17b, the upper gears 18 located on the washer 11 extend vertically downward to mate with the corresponding set of lower gears 19 when the flex-shaft 34 is inserted into the receiver 6. As previously discussed, each upper gear 18 has the circular open bottom 31 with the threaded portion 32 to mate with the corresponding lower gear 19. In turn, each lower gear 19 has the spear-like head 24 with oval shape to mate with the corresponding upper gear 18. In the preferred embodiment, the adapter 2 comprises four upper gears 18 and four corresponding lower gears 19. Alternatively, in an embodiment wherein the adapter is capable of having more than four flex-shafts, the number of upper and lower gears are equal to the number of flex-shafts.

Figure 18A:
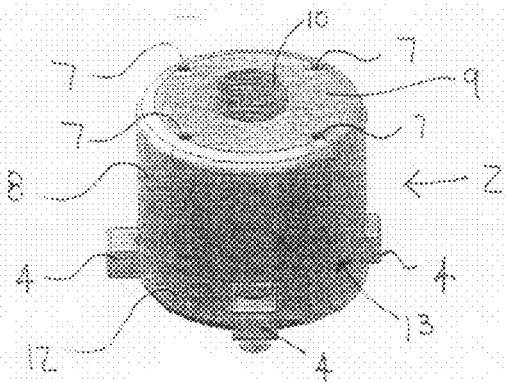
FIG. 18a is a perspective view in accordance with one embodiment of the present invention of the top of the adapter.
Figure 18B:
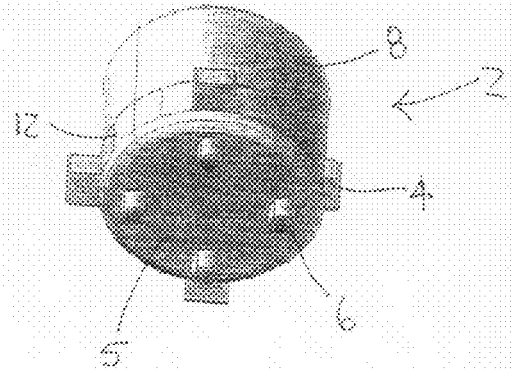
FIG. 18b is a perspective view in accordance with one embodiment of the present invention of the bottom of the adapter.
Figure 18C:
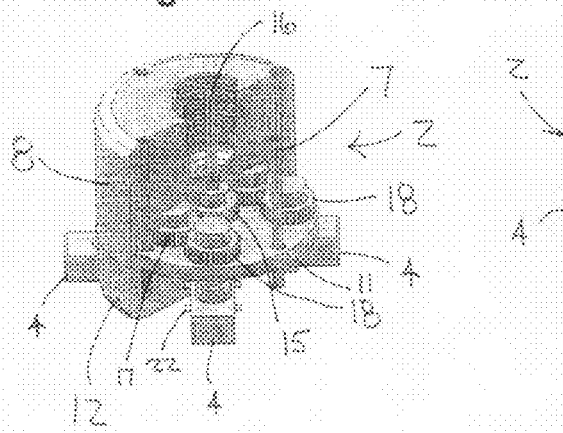
FIG. 18c is a perspective partial cross-sectional view in accordance with one embodiment of the present invention of the top of the adapter.
Figure 18D:
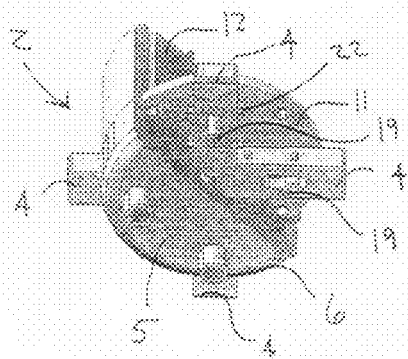
FIG. 18d is a perspective partial cross-sectional view in accordance with one embodiment of the present invention of the bottom of the adapter.

Turning to FIGS. 16a-16d, the switching members 4, lower gears 19 and block 39 in accordance with one embodiment of the present invention are disclosed. The block 39 has a cylindrical shape extending vertically to contact the main gear 15 (shown in FIG. 6d). The block 39 is located at the center of the lower portion 12 of the housing 3. In the preferred embodiment of this invention, the four switching members 4 contact the block 39 with the most forward face 38 of the member 4. The block 39 ensures that only the desired one of the plurality of flex-shafts 34 selected by the operator will acquire power from the drill 1 by preventing the members 4 corresponding to the other flex-shafts not selected by the operator from rising up causing the lower gears 19 to contact the upper gears 18 and, ultimately, acquire power from the drill 1. The lower gears 19 extend vertically through the slots 21 located on the members 4. Turning to FIG. 18d, the lower gears 19 extend vertically downward through the slots 21 directly over the receivers 6. The flex-shafts 34 are inserted into the receivers 6 to connect to the square opening 30 of the lower gear 19. In turn, the insertion of the flex-shaft 34 into the receiver overcomes the biasing mechanism 20 allowing the lower gear 19 to mate with the upper gear 18. In one embodiment, the biasing mechanism 20 is a spring.

In the preferred embodiment, an operator selects the desired drill bit for operation. The operator pushes a desired switching member 4 into the bottom portion 12 of the housing 3. The desired member 4 travels along the longitudinal recess 14 of the bottom portion 12 until the rods 22 fit into the guiding channels 23. The member 4 rises as the rods 22 travel vertically along the guiding channel 23. As the member 4 rises, the lower gear 19 corresponding to the desired member contacts the corresponding upper gear 18. Subsequently, the operator inserts the flex-shaft 34 into the receiver 6 to connect with the lower gear 19, which overcomes the biasing mechanism 20 and the lower gear 19 mates with the upper gear 18. Simultaneously, the block 39 prevents the members not selected by the operator from rising and, therefore, power is not transferred from the drill 1 to the flex-shafts 34 not selected.

In the preferred embodiment, electric power is applied to the drill 1, which rotates the drill chuck 28 and the post 16 attached to the chuck and connected to the main gear 15. In turn, the reverse gears 17 contacting the rotating main gear 15 rotate. As a result, the upper gears 18 contacting the rotating reverse gears rotate. The lower gear 19 extending through the selected member is mated with the rotating upper gears 18 and rotates. Accordingly, power is transferred to the flex-shaft 34 connected to the lower gear 19 and the operator is able to perform work with the desired nail bit.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A multiple flex-shaft adapter coupled to an electric drill having a drill chuck for performing specialized cosmetic functions for hands and fingernails, comprising:

a housing assembly attaching to the drill at one end and connecting at an opposite end to a plurality of flex-shafts;

a gear assembly in the housing assembly transferring power from the drill to a desired one of the plurality of flex-shafts, said gear assembly having a main gear connecting to a post engaging the drill chuck and a plurality of forward and reverse gears, said reverse gears engaging the main gear and further engaging the forward gears;

a plurality of switching members each corresponding to one of the plurality of flex-shafts, said plurality of switching members selectable to allow engagement of the desired one of the plurality of flex-shafts to the gear assembly;

a plurality of receivers positioned on the opposite end of the housing assembly for receiving a corresponding one of the plurality of flex-shafts such that each of the plurality of flex-shafts are capable of hanging from the housing assembly in an operationally ready position only requiring power from the drill upon selection of one of the plurality of switching members; and a block allowing power from the drill to transfer to only the desired one of the plurality of flex-shafts.

2. The adapter of claim 1, wherein said forward gears have an upper gear and a lower gear, said upper gear having an open bottom with internal ridges mating with said lower gear, said lower gear having a spear-like head mating with said upper gear and a square open bottom attaching to the flex-shaft.

3. The adapter of claim 2, wherein said housing assembly has top and bottom portions, said top portion having a threaded opening for receiving the drill at the one end, said bottom portion connecting at the opposite end to the plurality of flex-shafts and having diametrically opposed longitudinal recesses with a pair of guiding channels receivable in all of the recesses.

4. The adapter of claim 3, wherein said housing assembly further has a washer positioned between said top and bottom portions to secure the gear assembly.

5. The adapter of claim 3, wherein said plurality of switching members are operable to travel in the recesses until a pair of rods extending perpendicular to said members fit into the pair of guiding channels allowing said members to rise causing the lower gear to contact the upper gear.

6. A multiple flex-shaft adapter coupled to an electric drill having a drill chuck for performing specialized cosmetic functions for hands and fingernails, comprising:

a housing assembly attaching to the drill at one end and connecting at an opposite end to a plurality of flex-shafts;

a gear assembly in the housing assembly transferring power from the drill to a desired one of the plurality of flex-shafts, said gear assembly having a main gear attached to a post engaging the drill chuck and a plurality of forward and reverse gears, said reverse gears engaging the main gear and further engaging the forward gears, said forward gears having an upper gear corresponding to a lower gear; and a plurality of switching members selectable to allow engagement of the desired one of the plurality of flex-shafts to the gear assembly.

7. The adapter of claim 6, further having a plurality of receivers at the opposite end of the housing assembly wherein the plurality of flex-shafts insert into said housing assembly causing the gear assembly to engage and power to transfer from the drill through the gear assembly to the desired one of the plurality of flex-shafts.

8. The adapter of claim 6, further having a block located in the housing assembly allowing power from the drill to transfer to only the desired one of the plurality of flex-shafts.

9. The adapter of claim 6, wherein said housing assembly has top and bottom portions, said top portion connecting at the one end to the drill, said bottom portion connecting at the opposite end to the plurality of flex-shafts.

10. The adapter of claim 9, wherein said top portion further has a threaded opening on the one end for receiving the drill.

11. The adapter of claim 9, wherein said bottom portion further has diametrically opposed longitudinal recesses with a pair of guiding channels receivable in all of the recesses.

12. The adapter of claim 11, wherein said plurality of switching members are operable to travel in the recesses until a pair of rods extending perpendicular to said members fit into the pair of guiding channels allowing said members to rise causing the lower gear to contact the upper gear.

* * * * *